US007971492B2

(12) United States Patent
Wen et al.

(10) Patent No.: US 7,971,492 B2
(45) Date of Patent: Jul. 5, 2011

(54) METHOD AND SYSTEM FOR INSPECTING CHARACTERISTICS OF BENDED FLEXIBLE UNIT

(75) Inventors: Bor-Jiunn Wen, Hsinchu (TW); Cheng-Hsien Chen, Chiayi (TW); Zong-Ying Chung, Kaohsiung (TW); Hsin-Yi Ko, Taipei (TW); Ming-Chieh Huang, Taipei County (TW)

(73) Assignee: Industrial Technology Research Institute, Hsinchu (TW)

( * ) Notice: Subject to any disclaimer, the term of this patent is extended or adjusted under 35 U.S.C. 154(b) by 427 days.

(21) Appl. No.: 12/126,066

(22) Filed: May 23, 2008

(65) Prior Publication Data

US 2009/0272198 A1    Nov. 5, 2009

(30) Foreign Application Priority Data

May 2, 2008    (TW) ................................ 97116211 A

(51) Int. Cl.
*G01N 3/20* (2006.01)
(52) U.S. Cl. ........................................................ 73/849
(58) Field of Classification Search .................... 73/849, 73/159, 852
See application file for complete search history.

(56) References Cited

U.S. PATENT DOCUMENTS

| 4,904,901 A * | 2/1990 | Simopoulos et al. ......... 313/509 |
| 4,907,888 A * | 3/1990 | Clarke et al. .................. 356/613 |
| 5,461,893 A * | 10/1995 | Tyler .............................. 72/16.2 |
| 6,578,434 B1 * | 6/2003 | Maubant et al. ................ 73/849 |
| 6,980,291 B2 | 12/2005 | Saito |
| 7,036,364 B2 * | 5/2006 | Swillo et al. .................... 73/159 |
| 7,181,979 B1 | 2/2007 | Lin et al. |
| 7,278,323 B2 * | 10/2007 | Hartmann et al. .............. 73/761 |
| 2007/0138679 A1 * | 6/2007 | Lin et al. ...................... 264/40.1 |

FOREIGN PATENT DOCUMENTS

| CN | 1798956 A | 7/2006 |
| CN | 1963428 A | 5/2007 |

* cited by examiner

*Primary Examiner* — Lisa M Caputo
*Assistant Examiner* — Octavia Davis
(74) *Attorney, Agent, or Firm* — WPAT, PC; Justin King

(57) ABSTRACT

A method for inspecting characteristics of bended flexible unit is disclosed, which comprises steps of: (a) providing a clip unit, an observing unit, a characteristic-inspecting unit and a controlling unit; said clip unit, observing unit, and characteristic-inspecting unit are electrically connected to said controlling unit which stored a predetermined radius; (b) the clip unit clips a flexible unit and bends the same; (c) the observing unit gets the lateral profile of the flexible unit and sends it to the controlling unit which calculates the bending radius thereof accordingly; and (d) the controlling unit determines if the bending radius is the same to the predetermined one; if positive, the clip unit stops and the characteristic-inspecting unit inspects the characteristic of said flexible unit; if negative, the procedure returns to step (b).

32 Claims, 3 Drawing Sheets

METHOD AND SYSTEM FOR INSPECTING CHARACTERISTICS OF BENDED FLEXIBLE UNIT

FIELD OF THE INVENTION

The present invention relates to a method and system for inspecting characteristics of bended flexible unit.

BACKGROUND OF THE INVENTION

With rapid advance in semiconductor technology as well as in electronic display industry, the designs for all kinds of consumer electronic products, including cellular phones, notebook computers and other digital household appliances, are becoming more and more diversified while their lifespan are shorten as well. In addition, they are designed to be compact, portable, easy and comfort to use, and fashionable that all those innovated new designs is most welcomed by consumers and thus becoming the main stream in the market. However, it's a dilemma for any electronic devices to bring the right balance between the portability requirement for thinner, lighter and smaller products and the comfort in usage. For usage comfort, it is important for the electronic device to have a large display screen by which eyes of a user of the electronic device are likely to suffer less stress when he/she is reading messages from the display screen of the electronic device. Nevertheless, it usually may have difficulties to design an electronic device that is compact and with good portability, but the same time is configured with a large-sized display screen as it is limited by the flexibility of the display screen.

For overcoming the aforesaid dilemma, there are more and more manufacturers focusing their researches on the development of flexible units. Imaging that when all the parts used in an electronic device, such as a cellular phone or a notebook computer, are flexible units, such electronic device should be easy to carry around since it can be rolled up or folded even when it is configured with a large-sized display screen. Despite of the obvious advantage in flexible units, there are still many technical difficulties to be overcome before such flexible units to be realized and thus there is no mass-produced flexible unit available at the moment. Currently, in most sci-tech papers, the flexible unit is just a part that can be bended or flexed where at most there is a ruler provided for measuring an allowable bending radius of such flexible units. It is noted that there is no definition regarding to the flexibility of any flexible unit, nor is there any in-depth study or standard specification relating to the optical, mechanical and electrical characteristics of bended flexible units. Therefore, it is required to have a robust mechanism for not only defining the flexibility for flexible units in a quantification manner, but also for inspecting and evaluating the optical, mechanical and electrical characteristics of bended flexible units.

In U.S. Pat. No. 7,721,979, a method for inspecting flexible device is provided by which a flexible device is conveyed to pass through a plurality of rollers of different radiuses where it is bended into different bending states of different bending radiuses, and a performance inspection is performed on the flexible device for inspecting its electrical, optical, or opto-electric characteristics as it is being bended in different bending states. Although, by the aforesaid method, the apparatus for inspecting flexible devices can be integrated into the apparatus for manufacturing flexible devices, the performance inspection is not thorough enough since the radiuses of the rollers used in the inspection are fixed that it can only bend the flexible device into the curvatures conforming to those rollers and nothing more.

In U.S. Pat. No. 6,980,291, a method and apparatus for inspecting a curved shape are provided. The inspection apparatus is substantially an image capturing device integrated with a dot matrix light source comprising a plurality of dot light sources. Operationally, at first, an flexible device which is not bended is illuminated by the dot matrix light source so as to be imaged by the image capturing device while registering the resulting image into a memory device; and then, without changing the positioning of the image capturing device and the dot matrix light source, the imaging capturing device is enabled to pick up another imager of the flexible device when it is bended. As there are differences between the image of the flexible device that is not bended and the image of the bended flexible device and the two images are stored in the memory device which is accessible to a computer, the bending radius of the bended flexible device can be obtained by the calculation of the computer using the two images. However, although the aforesaid method can be used for obtaining the bending radius of a bended flexible device, it usually provides no effective means for bending the flexible device into different bending states so as to be applied in actual practice for inspecting characteristics of the flexible device. Thus, it is usually difficult to built a lookup table relating the optical, mechanical and electrical characteristics of a bended flexible unit to its bending states.

Therefore, the invention provides a method and system for inspecting characteristics of bended flexible units that are free from the aforesaid shortcomings.

SUMMARY OF THE INVENTION

It is the object of the present invention to provide a method with ability for quantifying the bending of a flexible unit, capable of inspecting and evaluating the characteristics of the bended flexible units.

To achieve the above object, the present invention provides a method for inspecting characteristics of bended flexible units, which comprises the steps of: (a) providing a clip unit, an observing unit, a characteristic-inspecting unit and a controlling unit while electrically connecting the clip unit, the observing unit, and the characteristic-inspecting unit with the controlling unit and further storing a predetermined radius in the controlling unit; (b) using the clip unit to clip a flexible unit so as to bend the same; (c) directing the observing unit to capture the lateral profile of the flexible unit and then sending the captured profile to the controlling unit for calculating and thus obtaining the bending radius of the bended flexible unit accordingly; and (d) using the controlling unit to make an evaluation to determine whether the bending radius is the same as the predetermined radius; if so, the clip unit is stopped and the characteristic-inspecting unit is activated for inspecting the characteristic of the flexible unit; otherwise, the procedure returns to step (b).

In the other embodiment, the present invention further provides a method for inspecting characteristics of bended flexible units, comprising the steps of: providing a clip unit, an observing unit, a characteristic-inspecting unit and a controlling unit while electrically connecting the clip unit, the observing unit, and the characteristic-inspecting unit with the controlling unit and further storing a predetermined radius in the controlling unit; using the clip unit to clip a flexible unit so as to bend the same; directing the observing unit to capture the lateral profile of the flexible unit and then sending the captured profile to the controlling unit for calculating and thus obtaining the bending radius of the bended flexible unit accordingly while enabling the characteristic-inspecting unit to inspect the characteristic of the flexible unit which are then being sent to the controlling unit; and enabling the controlling unit to establish a lookup table relating the characteristics to bending radiuses by pairing the inspected characteristics to its corresponding bending radiuses.

In addition, the present invention further provides a system for inspecting characteristics of a flexible unit, which comprises: a controlling unit, for calculating the bending radius of the flexible unit; a clip unit, electrically connected to the controlling unit and used for clipping the flexible unit so as to bend the same; an observing unit, electrically connected to the controlling unit and used for capturing the lateral profile of the flexible unit; and a characteristic-inspecting unit, electrically connected to the controlling unit and used for inspecting the characteristic of the flexible unit; wherein the controlling unit is enabled to establish a lookup table relating the characteristics to bending radiuses by pairing the inspected characteristics to its corresponding bending radiuses.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention and wherein.

DESCRIPTION OF THE EXEMPLARY EMBODIMENTS

For your esteemed members of reviewing committee to further understand and recognize the fulfilled functions and structural characteristics of the invention, several exemplary embodiments cooperating with detailed description are presented as the follows.

Figure 1:
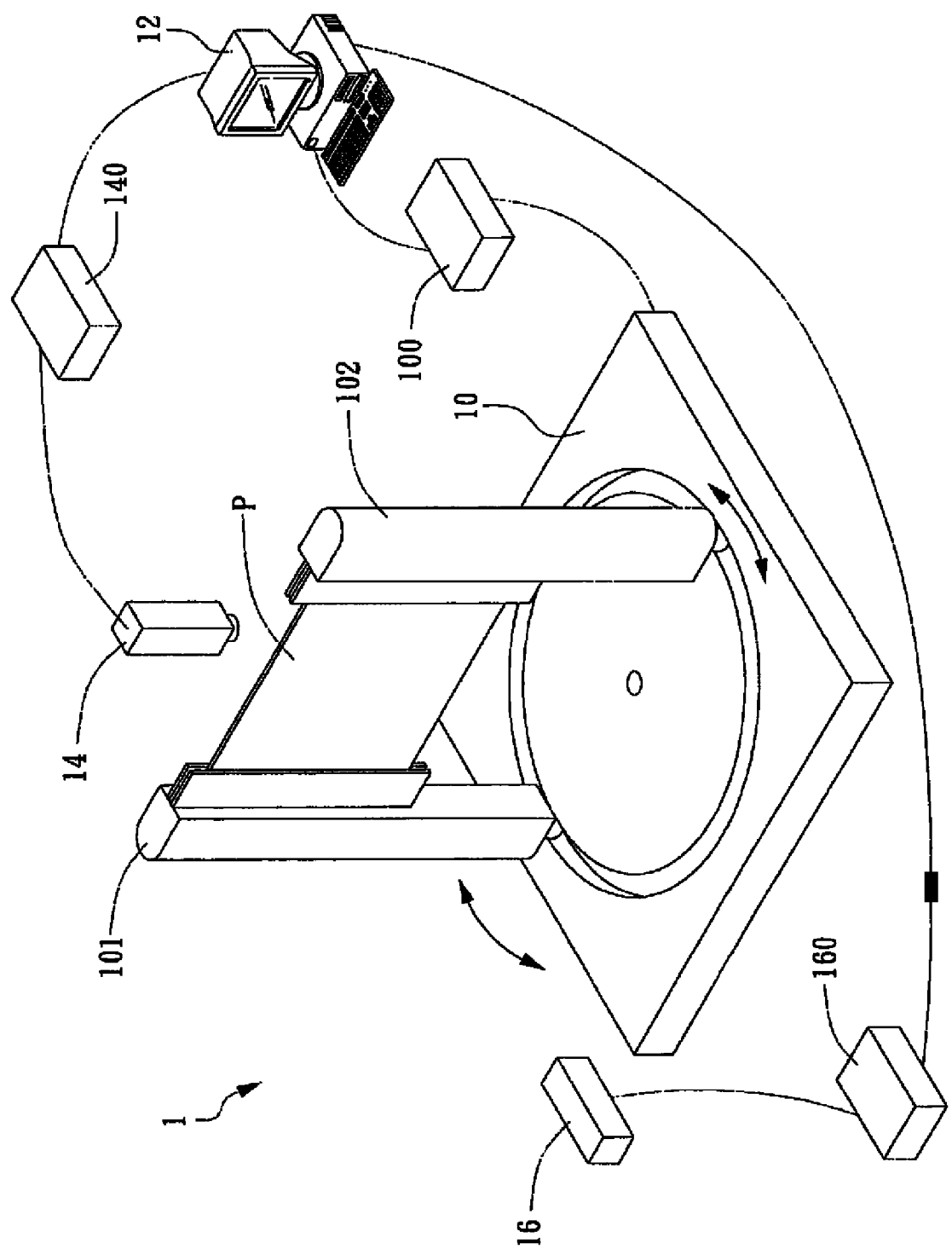
FIG. 1 shows a system for inspecting characteristics of a flexible unit according to an exemplary embodiment of the invention.

Please refer to FIG. 1, which shows a system for inspecting characteristics of a flexible unit according to an exemplary embodiment of the invention. As shown in FIG. 1, the system for inspecting characteristics of flexible units 1 is comprises of: a clip unit 10, a computer 12, a CCD camera 14 and a characteristic-inspecting unit 16. Wherein, the clip unit 10 is electrically connected to the computer 12 through a movement controller 100; the CCD camera 14 is also electrically connected to the computer 12 through another movement controller 140; and the characteristic-inspecting unit 16 is also electrically connected to the computer 12 through yet another movement controller 160. Thus, the computer 12 is able to control the movements of the clip unit 10, the CCD camera 14 and the characteristic-inspecting unit 16 through the three movement controllers 100, 140, 160 in respective. In addition, the clip unit 10 is configured with two clipping arms 101, 102 which can work cooperatively for holding a flexible panel P. In this embodiment, the flexible panel P is a sheet-like or plate-like object.

Operationally, the computer 12 will direct the movement controller 140 to move the CCD camera 14 to a side of the flexible panel P for enabling the CCD camera 14 to pick up the lateral profile the flexible panel P and then send the captured image back to the computer 12. Moreover, the computer 12 is also capable of directing the movement controller 160 to move the characteristic-inspecting unit 16 to a location in the vicinity of the flexible panel P, i.e. for positioning the characteristic-inspecting unit 16 at a specific distance away from the surface, the side, or any arbitrary position of the flexible panel P, so that the characteristic-inspecting unit 16 is able to inspect the characteristic of the flexible panel P, such as an optical property (brightness, chromaticity), a mechanical property (surface defect, deformation), and/or electrical property.

Figure 2:
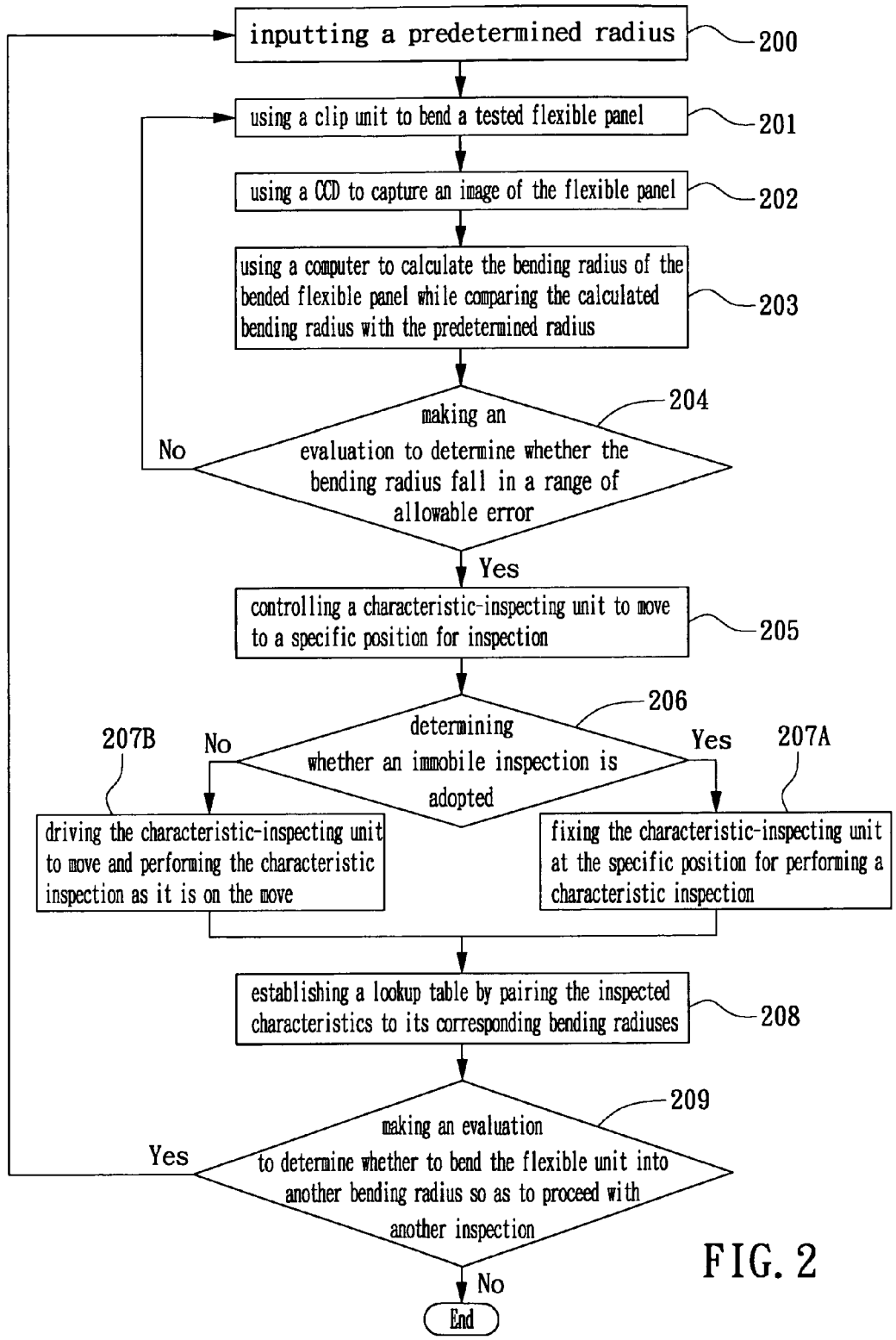
FIG. 2 is a flow chart depicting steps of a method for inspecting characteristics of flexible units according to an exemplary embodiment of the invention.

Please refer to FIG. 2, which is a flow chart depicting steps of a method for inspecting characteristics of a flexible unit according to a first exemplary embodiment of the invention. In this first embodiment, the method for inspecting characteristics of flexible units comprises the following steps:

Step 200: inputting a predetermined radius into the computer;

Step 201: using the computer to control the clip unit to bend a tested flexible panel where as the flexible panel is being clipped by the clip unit;

Step 202: using the CCD camera to capture an lateral profile image of the flexible panel;

Step 203: sending the lateral profile image to the computer where it is processed so as to obtain the bending radius of the bended flexible panel while comparing the obtained bending radius with the predetermined radius;

Step 204: enabling the computer to make an evaluation to determine whether the bending radius fall in a range of allowable error; of so, the flow proceeds to step 205; otherwise, the flow returns back to step 201 in a feedback control manner;

Step 205: using the computer for directing the characteristic-inspecting unit to move to a location in the vicinity of the flexible panel for preparing the same to carry on a characteristic inspection;

Step 206: determining whether an immobile inspection is adopted; if so, the flow proceeds to step 207A; otherwise, the flow proceeds to step 207B;

Step 207A: fixing the characteristic-inspecting unit at the specific position for performing an optical/mechanical/electrical characteristic inspection;

Step 207B: driving the characteristic-inspecting unit to move and performing an optical/mechanical/electrical characteristic inspection as it is on the move;

Step 208: establishing a lookup table by pairing the inspected optical/mechanical/electrical characteristics to its corresponding bending radiuses; and Step 209: making an evaluation to determine whether to bend the flexible unit into another bending radius so as to proceed with another inspection; if so, the flow proceeds back to step 200; otherwise, the flow stops.

Figure 3:
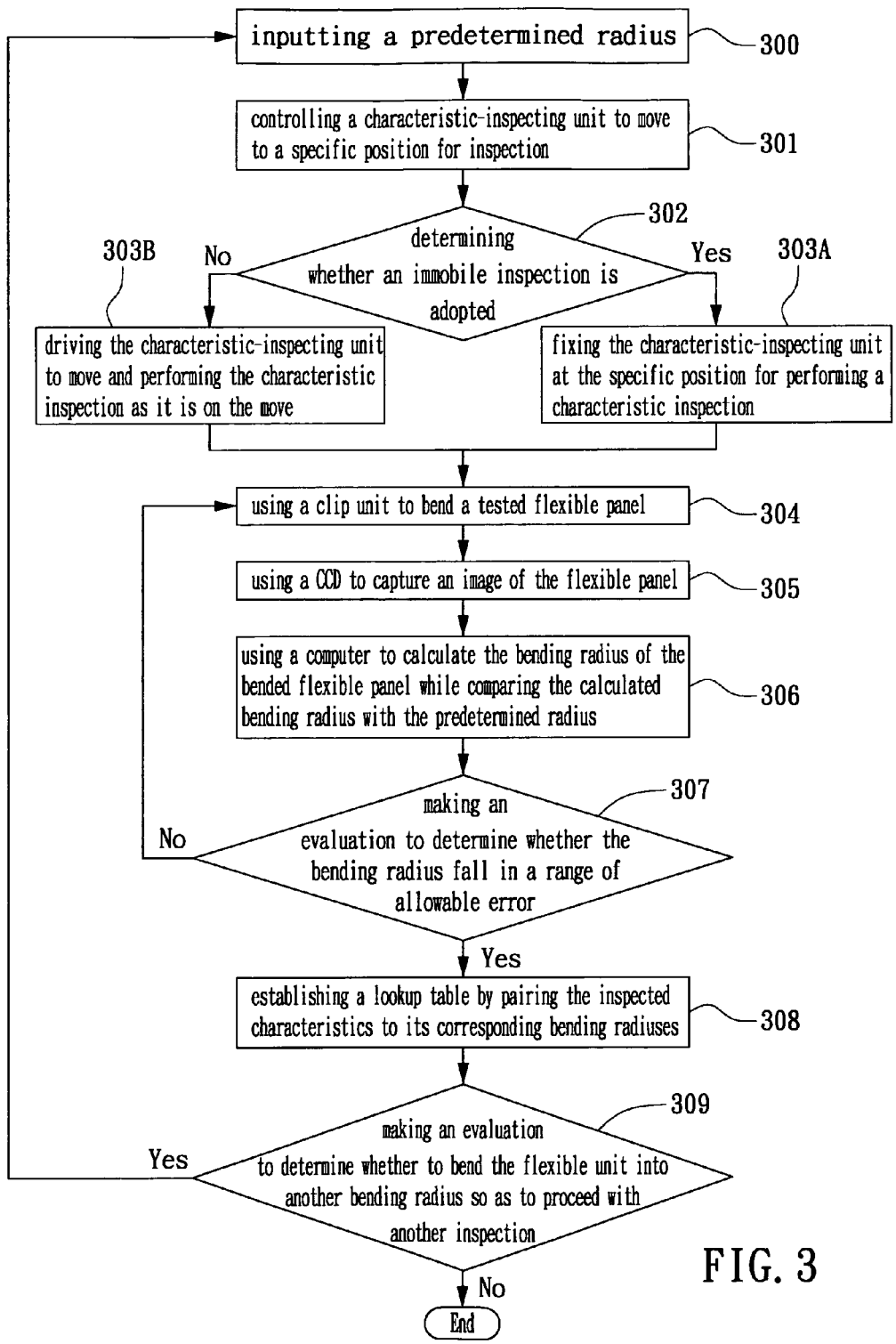
FIG. 3 is a flow chart depicting steps of a method for inspecting characteristics of flexible units according to another exemplary embodiment of the invention.

Please refer to FIG. 3, which is a flow chart depicting steps of a method for inspecting characteristics of a flexible unit according to a second exemplary embodiment of the invention. In this second embodiment, the method for inspecting characteristics of flexible units comprises the following steps:

Step 300: inputting a predetermined radius into the computer;

Step 301: using the computer for directing the characteristic-inspecting unit to move to a location in the vicinity of the flexible panel for preparing the same to carry on a characteristic inspection;

Step 302: determining whether an immobile inspection is adopted; if so, the flow proceeds to step 303A; otherwise, the flow proceeds to step 303B;

Step 303A: fixing the characteristic-inspecting unit at the specific position for performing an optical/mechanical/electrical characteristic inspection;

Step 303B: driving the characteristic-inspecting unit to move and performing an optical/mechanical/electrical characteristic inspection as it is on the move;

Step 304: using the computer to control the clip unit to bend a tested flexible panel where as the flexible panel is being clipped by the clip unit;

Step 305: using the CCD camera to capture an lateral profile image of the flexible panel;

Step 306: sending the lateral profile image to the computer where it is processed so as to obtain the bending radius of the bended flexible panel while comparing the obtained bending radius with the predetermined radius;

Step 307: enabling the computer to make an evaluation to determine whether the bending radius fall in a range of allowable error; of so, the flow proceeds to step 308; otherwise, the flow returns back to step 304 in a feedback control manner;

Step 308: establishing a lookup table by pairing the inspected optical/mechanical/electrical characteristics to its corresponding bending radiuses; and Step 309: making an evaluation to determine whether to bend the flexible unit into another bending radius so as to proceed with another inspection; if so, the flow proceeds back to step 300; otherwise, the flow stops.

To sum up, the present invention provides a mechanism capable of bending a flexible unit into any arbitrary curvature at will so as to inspect its bending radius in a quantitative manner. With the aforesaid method and system, the present invention provides a robust mechanism with ability for quantifying the bending of a flexible unit, which is capable of inspecting and evaluating the optical, mechanical and electrical characteristics of the bended flexible units. Such mechanism is very helpful in the reliability test of any manufacturing process.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for inspecting characteristics of flexible units, comprising the steps of:
   (a) providing a clip unit, an observing unit, a characteristic-inspecting unit and a controlling unit while electrically connecting the clip unit, the observing unit, and the characteristic-inspecting unit with the controlling unit and further storing a predetermined radius in the controlling unit;
   (b) using the clip unit to clip a flexible unit so as to bend the same;
   (c) directing the observing unit to capture the lateral profile of the flexible unit and then sending the captured profile to the controlling unit for calculating and thus obtaining a bending radius of the bended flexible unit accordingly; and
   (d) using the controlling unit to make an evaluation to determine whether the bending radius is the same as the predetermined radius;
      if so, the clip unit is stopped and the characteristic-inspecting unit is activated for inspecting the characteristic of the flexible unit;
      otherwise, the procedure returns to step (b).

2. The method of claim 1, further comprising the step of:
   (e) enabling the controlling unit to establish a lookup table relating the characteristics to bending radiuses by pairing the inspected characteristics to its corresponding bending radiuses.

3. The method of claim 1, wherein the observing unit is a charge-coupled device (CCD) camera.

4. The method of claim 1, wherein the bending radius in the step (c) is obtained by a calculation basing upon any three arbitrary points selected from the lateral profile by the controlling unit.

5. The method of claim 1, wherein the flexible unit is a plate-like object.

6. The method of claim 1, wherein the characteristic of the flexible unit to be inspected is an optical property.

7. The method of claim 6, wherein the optical property is brightness.

8. The method of claim 6, wherein the optical property is chromaticity.

9. The method of claim 1, wherein the characteristic of the flexible unit to be inspected is a mechanical property.

10. The method of claim 9, wherein the mechanical property is surface defect.

11. The method of claim 9, wherein the mechanical property is deformation.

12. The method of claim 1, wherein the characteristic of the flexible unit to be inspected is an electrical property.

13. A method for inspecting characteristics of flexible units, comprising the steps of:
   providing a clip unit, an observing unit, a characteristic-inspecting unit and a controlling unit while electrically connecting the clip unit, the observing unit, and the characteristic-inspecting unit with the controlling unit;
   using the clip unit to clip a flexible unit so as to bend the same;
   directing the observing unit to capture the lateral profile of the flexible unit and then sending the captured profile to the controlling unit for calculating and thus obtaining the bending radius of the bended flexible unit accordingly while enabling the characteristic-inspecting unit to inspect the characteristic of the flexible unit which are then being sent to the controlling unit; and
   enabling the controlling unit to establish a lookup table relating the characteristics to bending radiuses by pairing the inspected characteristics to its corresponding bending radiuses.

14. The method of claim 13, wherein the observing unit is a charge-coupled device (CCD) camera.

15. The method of claim 13, wherein the bending radius in the step (c) is obtained by a calculation basing upon any three arbitrary points selected from the lateral profile by the controlling unit.

16. The method of claim 13, wherein the flexible unit is a plate-like object.

17. The method of claim 13, wherein the characteristic of the flexible unit to be inspected is an optical property.

18. The method of claim 17, wherein the optical property is brightness.

19. The method of claim 17, wherein the optical property is chromaticity.

20. The method of claim 13, wherein the characteristic of the flexible unit to be inspected is a mechanical property.

21. The method of claim 20, wherein the mechanical property is surface defect.

22. The method of claim 20, wherein the mechanical property is deformation.

23. The method of claim 13, wherein the characteristic of the flexible unit to be inspected is a mechanical property.

24. A system for inspecting characteristics of flexible units, comprising:
   a controlling unit, for calculating the bending radius of a flexible unit and said flexible unit is a plate-like object;
   a clip unit, electrically connected to the controlling unit and used for clipping the flexible unit so as to bend the same;
   an observing unit, electrically connected to the controlling unit and used for capturing the lateral profile of the flexible unit; and
   a characteristic-inspecting unit, electrically connected to the controlling unit and used for inspecting the characteristic of the flexible unit;
   wherein the controlling unit has a predetermined radius stored therein and is enabled to establish a lookup table relating the characteristics to bending radiuses by pairing the inspected characteristics to its corresponding bending radiuses;
   wherein the clip unit is stopped and the characteristic-inspecting unit is activated for inspecting the characteristic of the flexible unit when the controlling unit determines whether the bending radius of the flexible unit is the same as the predetermined radius, and the observing unit captures the lateral profile of the flexible unit and sends the captured lateral profile to the controlling unit for calculating the bending radius of the bent flexible unit.

25. The system of claim 24, wherein the observing unit is a charge-coupled device (CCD) camera.

26. The system of claim 24, wherein the characteristic of the flexible unit to be inspected is an optical property.

27. The system of claim 26, wherein the optical property is brightness.

28. The system of claim 26, wherein the optical property is chromaticity.

29. The system of claim 24, wherein the characteristic of the flexible unit to be inspected is a mechanical property.

30. The system of claim 29, wherein the mechanical property is surface defect.

31. The system of claim 29, wherein the mechanical property is deformation.

32. The system of claim 24, wherein the characteristic of the flexible unit to be inspected is a mechanical property.

* * * * *